(12) United States Patent
Rodefeld et al.

(10) Patent No.: US 6,198,007 B1
(45) Date of Patent: Mar. 6, 2001

(54) PROCESS FOR THE PREPARATION OF 1-SUBSTITUTED 2,4-DINITROBENZENES

(75) Inventors: Lars Rodefeld, Leverkusen; Alexander Klausener, Pulheim; Ferdinand Hagedorn, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/546,511

(22) Filed: Apr. 11, 2000

(30) Foreign Application Priority Data

Apr. 22, 1999 (DE) .............................. 199 18 291

(51) Int. Cl.[7] .................................................. C07C 205/00
(52) U.S. Cl. .......................... 568/584; 568/585; 568/586; 568/587
(58) Field of Search .................... 568/584, 585, 568/586, 587

(56) References Cited

U.S. PATENT DOCUMENTS

| 2,988,571 | 6/1961 | MacFie et al. | 260/613 |
|---|---|---|---|
| 4,125,367 | 11/1978 | Bugaut et al. | 8/11 |
| 4,259,261 | 3/1981 | Bugau et al. | 564/99 |
| 4,329,504 | 5/1982 | Bugau et al. | 564/443 |
| 4,686,301 | 8/1987 | Papenfuhs et al. | 549/427 |
| 4,695,656 | 9/1987 | Reh et al. | 568/587 |
| 5,399,773 | 3/1995 | Beitzke et al. | 568/30 |

FOREIGN PATENT DOCUMENTS

| 479831 | 7/1929 | (DE) . |
| 204111 | 12/1986 | (EP) . |
| 1591663 | 6/1981 | (GB) . |
| 1597034 | 9/1981 | (GB) . |

OTHER PUBLICATIONS

J. Chem. Soc. , 1921, (119) pp. 2076–2078, A New Synthesis of Oxazines, Fairbourne et al.

Primary Examiner—Samuel Barts
(74) Attorney, Agent, or Firm—Joseph C. Gil; Diderico van Eyl

(57) ABSTRACT

Provided is a process for the preparation of specific 1-substituted 2,4-dinitrobenzenes by reaction of 1-halogeno-2,4-dinitrobenzenes with mono-alkali metal salts of specific diols, in which the 1-halogeno-2,4-dinitrobenzene and the mono-alkali metal salt of the diol are simultaneously added and reacted.

19 Claims, No Drawings

PROCESS FOR THE PREPARATION OF 1-SUBSTITUTED 2,4-DINITROBENZENES

BACKGROUND OF THE INVENTION

The present invention relates to a process for the preparation of 1-substituted 2,4-dinitrobenzenes by reacting 1-halogeno-2,4-dinitrobenzenes with mono-alkali metal salts of diols.

1-substituted 2,4-dinitrobenzenes are used in many different areas. Their synthesis is therefore of particular importance. 2-(2',4'-dinitro-phenoxy)-ethanol is, for example, a suitable starting material for the preparation of 2-(2',4'-diaminophenoxy)-ethanol and its salts, which are used in oxidation dye compositions as meta components (DE-A-2,758,735 and DE-A-2,737,138). 2-(2',4'-dinitrophenoxy)-ethanol is also an excellent plasticizer for cellulose acetate.

According to DE-A-2,758,735, the preparation of 2-(2',4'-dinitrophenoxy)-ethanol starts from an initial charge of mono-potassium glycolate in ethylene glycol, to which 1-chloro-2,4-dinitrobenzene is added. The mono-potassium glycolate is present in a 1.4-fold molar excess. However, this process produces 2-(2',4'-dinitrophenoxy)-ethanol only in a yield of 68.6%. From the fact that the melting point of the resulting product is given as 100–102° C., while pure, crystalline 2-(2',4'-dinitrophenoxy)-ethanol has, according to German Patent Specification 479,831, a melting point of 111–112° C., it can be concluded that the product from DE-A-2,758,735 also contains significant impurities.

J. Chem. Soc. 1921 (119), 2076–8 discloses a further process for the preparation of 2-(2',4'-dinitrophenoxy)-ethanol, in which a solution of 1-chloro-2,4-dinitrobenzene in ethylene glycol is the initial charge and a mixture of sodium hydroxide, water and ethylene glycol is metered into this initial charge. The mixture of sodium hydroxide, water and ethylene glycol is obtained by dissolving the solid sodium hydroxide in water and then adding the ethylene glycol. Using this process, a crude yield of 93% is achieved, in which the crude product is subsequently subjected to recrystallization from acetic acid for purification of the 2-(2',4'-dinitrophenoxy)-ethanol. In this reaction, the undesired by-product 1,2-bis-(2',4'-dinitrophenoxy)-ethane forms. Experiments are also described in which the mixture of sodium hydroxide, water and ethylene glycol is not prepared by adding the ethylene glycol to the aqueous sodium hydroxide solution, but, vice versa, by adding the aqueous sodium hydroxide solution to the ethylene glycol. It is stated that, as a result, the formation of the by-product 1,2-bis-(2',4'-dinitrophenoxy)-ethane can be avoided. However, a reworking of these experiments showed that even in this variant 1,2-bis-(2',4'-dinitrophenoxy)-ethane forms as 8% of the total yield.

U.S. Pat. No. 2,988,571 describes a process for the preparation of 2-(2',4'-dinitrophenoxy)-ethanol, in which the formation of the by-product 1,2-bis-(2',4'-dinitrophenoxy)-ethane and 1,2-bis-(2',4'-dinitrophenoxy)-ethanol is said to be repressed. For this purpose, 1-chloro-2,4-dinitrobenzene and solid, powdered, largely anhydrous sodium hydroxide, each in small portions, are simultaneously metered in to an initial charge of ethylene glycol at temperatures of 30–130° C., preferably 85–90° C. An important factor here is that fresh portions of the two substances are in each case only added again when the previously added portions have reacted completely. A decisive factor is also that the molar ratio of the ethylene glycol to the 1-chloro-2,4-dinitrobenzene is at least 3, and the molar ratio of the 1-chloro-2,4-dinitrobenzene to the sodium hydroxide is about 1.1–1.3. Then, water is added to the reaction system in an amount such that the 2-(2',4'-dinitrophenoxy)-ethanol is produced as a precipitate. In a preferred embodiment of the process, a large number of extremely small portions is added, such that a quasi continuous addition of the 1-chloro-2,4-dinitrobenzene and of the sodium hydroxide results. In this way, a yield of 86.5% of 2-(2',4'-dinitrophenoxy)-ethanol, based on the 1-chloro-2,4-dinitrobenzene used, is obtained. However, despite this the reaction product contains about 8% of the by-product 1,2-bis-(2',4'-dinitrophenoxy)-ethane (Test 1). If the molar ratio of the 1-chloro-2,4-dinitrobenzene to the sodium hydroxide is increased beyond the given range, the proportion of the by-product 1,2-bis-(2',4'-dinitrophenoxy)-ethane even increases to 23% (Test 2).

Particularly when 1-substituted 2,4-dinitrobenzenes such as 2-(2',4'-dinitrophenoxy)-ethanol, are used in the cosmetics sector, e.g., as precursor compounds in the field of hair cosmetics, the purity of the 1-substituted 2,4-dinitrobenzenes is an important factor: even slight contamination by foreign substances is problematical for medicinal reasons (e.g., danger of triggering allergies).

The object of the present invention is therefore to provide a process which permits the preparation of 1-substituted 2,4-dinitrobenzenes and in particular of 2-(2',4'-dinitrophenoxy)-ethanol not only with very good yields, but also with high purities.

DESCRIPTION OF THE INVENTION

The above-named object is achieved by a process for the preparation of a 1-substituted 2,4-dinitrobenzene of the formula (I)

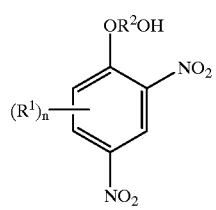

(I)

in which each $R^1$ is a linear or branched $C_1$–$C_{20}$-alkyl group, a $C_6$–$C_{18}$-aryl group, a $C_2$–$C_{20}$-acyl group, a COOH group, a $COOR^3$ group, in which $R^3$ is a linear or a branched $C_1$–$C_{20}$-alkyl radical, a $SO_3H$ group, a $SO_3R^4$ group, in which $R^4$ is a linear or a branched $C_1$–$C_{20}$-alkyl radical or a $C_6$–$C_{18}$-aryl radical in which one or more carbon atoms are optionally replaced by O, S or N, or $N(R^5)_2$, in which each $R^5$ is hydrogen, a linear or a branched $C_1$–$C_{20}$-alkyl radical or a $C_2$–$C_{20}$-acyl radical, n is an integer from 0 to 3, and $R^2$ is a radical of the formula (II)

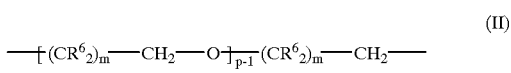

(II)

in which each $R^6$ is hydrogen or a $C_1$–$C_5$-alkyl radical, m is an integer from 1 to 12 and p is an integer from 1 to 4, or a radical of the formula (III),

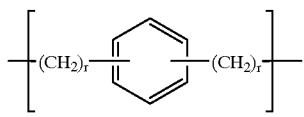

(III)

in which each r is an integer from 0 to 2 and one or more carbon atoms of the phenyl ring are optionally replaced by N, O or S.

The process generally involves the step of simultaneously reacting a 1-halogeno-2,4-dinitrobenzene of the formula (IV)

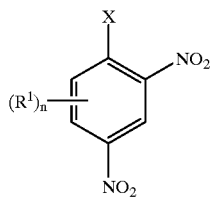

(IV)

in which X is halogen, and $R^1$ and n have the meanings given for the formula (I), with mono-alkali metal salts of a diol of the formula (V)

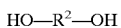 (V)

in which $R^2$ has the meaning given for the formula (I), characterized in that the halogeno-2,4-dinitrobenzene of the formula (IV) and the mono-alkali metal salt of the diol of the formula (V) are simultaneously added and reacted.

It is noteworthy that the process according to the invention with its essential simultaneous addition, e.g., metering, procedure of the 1-halogeno-2,4-dinitrobenzene of the formula (IV) and the mono-alkali metal salt of the diol of the formula (V) produces the 1-substituted 2,4-dinitrobenzenes of the formula (I) with a purity of at least 90%, preferably at least 92% and a yield of at least 88%. Recrystallization, as described in J. Chem. Soc. 1921 (119), 2076–8, is no longer necessary.

In the 1-halogeno-2,4-dinitrobenzenes of the formula (IV), X is preferably fluorine, chlorine, bromine or iodine, in particular chlorine. Each $R^1$ is preferably a linear or a branched $C_1$–$C_{10}$-alkyl group, a $C_6$–$C_{12}$-aryl group, a $C_2$–$C_6$-acyl group or a $N(R^5)_2$ group in which each $R^5$ is hydrogen, a linear or branched $C_1$–$C_6$-alkyl radical or a $C_2$–$C_6$-acyl radical. In addition, n is preferably 0, 1 or 2.

Some of the 1-halogeno-2,4-dinitrobenzenes of the formula (IV) used in the process according to the invention are available commercially or can be prepared in a manner known to the person skilled in the art. They can be metered in as melts, solids or as solutions in an organic solvent, herein referred to as organic solvent "A." Suitable organic solvents A are ethers, optionally substituted aliphatic hydrocarbons such as nitroalkanes or methylene chloride, optionally substituted aromatic hydrocarbons such as toluene, nitroaromatics or chloroaromatics, amides and ethylene glycol. N,N-dimethylacetamide, methylene chloride and tetrahydrofuran have proven particularly advantageous.

In the process according to the invention, mono-alkali metal salts of diols of the formula (V) are preferably the mono-sodium, mono-potassium or mono-caesium salts. In particular, the mono-sodium salts are used. $R^2$ is preferably a radical of the formula (II), in which m is an integer from 1 to 9, in particular 1, 2 or 3, $R^6$ is hydrogen or methyl, and p is 1 or 2. The radical $R^2$ is particularly preferably —[$CH_2$—$CH_2$]—, —[$CH(CH_3)$—$CH_2$]— or —[$CH_2$—$C(CH_3)_2$—$CH_2$]—, in which p is 1.

$R^2$ is also preferably a radical of the formula (III), in which r is 0 or 1. The radical $R^2$ is particularly preferably

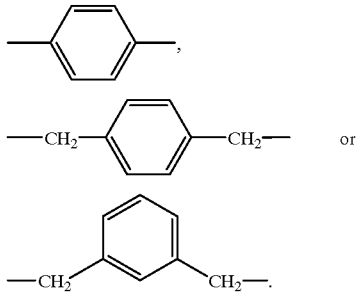

Preferably, the mono-alkali metal salt of the diol of the formula (V) is mono-potassium ethylene glycolate and in particular mono-sodium ethylene glycolate.

In a preferred embodiment of the process according to the invention, the mono-alkali metal salt of the diol of the formula (V) is used with a solvent in a mixture.

The preparation of the mono-alkali metal salts of diols of the formula (V) is known to the person skilled in the art and is usually carried out by reacting the diol of the formula (V) with an alkali metal hydroxide, in which the molar ratio between the diol and the alkali metal hydroxide is at least 2:1, preferably 2:1–20:1, and more preferably 10:1–20:1. Here, the excess diol of the formula (V) is, for example, introduced initially, and the alkali metal hydroxide is metered in. In this way, the mono-alkali metal salt of the diol is obtained with the diol (V) as the solvent as a mixture and can be used directly in the process according to the invention.

It has also proven successful, in the preparation of the mono-alkali metal salts of the diol of the formula (V) to introduce, not only the excess diol, but also an organic solvent, herein referred to organic solvent "B," and then to add the alkali metal hydroxide. This procedure is particularly advantageous when the organic solvent B can be used for the azeotropic drying of the reaction mixture. Suitable organic solvents B are ethers, optionally substituted aliphatic hydrocarbons such as nitroalkanes or methylene chloride, optionally substituted aromatic hydrocarbons such as toluene, nitroaromatics or chloroaromatics, amides and ethylene glycol. N,N-dimethylacetamide, methylene chloride and tetrahydrofuran have proven particularly advantageous. After the reaction, some or all of the organic solvent B can be removed by distillation. If all of the organic solvent B is removed, the mono-alkali metal salt of the diol (V) is in turn obtained in the mixture with the excess diol (V). If only some of the organic solvent B is removed, the mono-alkali metal salt of the diol (V) is accordingly in a mixture of diol (V) and organic solvent B and can be used directly in the process according to the invention in this form.

For implementation of the process according to the invention, it is advantageous if the mixture of the mono-alkali metal salt of the diol of the formula (V) and the diol of the formula (V), and optionally the organic solvent B, has a water content of less than 5%, preferably less than 2% and particularly preferably less than 0.2%.

The phrases "simultaneous addition," "simultaneously added," and equivalent phrases, herein also refer to either the 1-halogeno-2,4-dinitrobenzene of the formula (IV) or the mono-alkali metal salt of the diol of the formula (V) being added, per unit time, in an excess of at most 20 mol %, preferably at most 10 mol % and in particular at most 5 mol %, based on the other reactants in each case. From this, accordingly, it follows that it is possible that up to 20 mol %, preferably up to 10 mol % and in particular up to 5 mol % of the mono-alkali metal salt of the diol or of the 1-halogeno-2,4-dinitrobenzene are initially charged to the reaction vessel.

The molar ratio of the 1-halogeno-2,4-dinitrobenzene of the formula (IV) to the mono-alkali metal salt of the diol of the formula (V) is 1:1.05 to 1:2, preferably 1:1.1.

The process according to the invention is usually carried out at a temperature that ranges from 20 to 130° C., preferably from 40 to 80° C. and particularly preferably from 60 to 70° C. It has proven advantageous to carry out, after the metered addition with stirring, a post-reaction at a temperature that ranges from 20 to 80° C. over a period of up to 300 minutes.

In a further preferred embodiment of the process according to the invention, the 1-halogeno-2,4-dinitrobenzene of the formula (IV) and the mono-alkali metal salt of the diol of the formula (V) are metered into an initial charge of an organic solvent, herein referred to organic solvent "C." In this embodiment, it is particularly advantageous for the mono-alkali metal salt of the diol (V) to be used as a mixture with the diol (V) and optionally the organic solvent B, and for the initially charged organic solvent C to be identical to the diol (V) or the organic solvent B. If the mono-alkali metal salt of the diol has a radical $R^2$ of the formula (II), the initially charged organic solvent C is then preferably the appropriate diol of the formula (V) with the same radical $R^2$ of the formula (II). In principle, suitable solvents C also include ethers, optionally substituted aliphatic hydrocarbons such as nitroalkanes or methylene chloride, optionally substituted aromatic hydrocarbons such as toluene, nitroaromatics or chloroaromatics, amides and ethylene glycol. N,N-dimethylacetamide, methylene chloride and tetrahydrofuran have proven advantageous. It has also proven successful to carry out the reaction under inert gas.

The prepared 1-substituted 2,4-dinitrobenzene of the formula (I) is usually isolated following the reaction of the two starting materials by adding water to the reaction mixture and separating off the precipitated product.

The process according to the invention can be carried out either in one reactor or in two successive reactors. In the latter case, the first reactor is used mainly for metering in the two starting materials and the second reactor is used mainly for adding water for the purpose of precipitating the desired 1-substituted 2,4-dinitrobenzene.

The invention provides previously unavailable advantages. Unlike the process disclosed in DE-A-2,758,735, discussed in the Background of the Invention, for instance, Applicants' process produces reaction products with significantly less impurities. Unlike the process taught in J. Chem. Soc. 1921 (119), 2076–8 and U.S. Pat. No. 2,988,571, also discussed in the Background of the Invention, Applicants process avoids the formation of any appreciable amounts of undesired by-products such as 1,2-bis-(2',4'-dinitrophenoxy)-ethane. Also, recrystallization, as described in J. Chem. Soc. 1921 (119), 2076–8, is no longer necessary. As such, the invention provides the industry with a valuable process for making an important class of compounds.

The invention is further illustrated but is not intended to be limited by the following examples in which all parts and percentages are by weight unless otherwise specified.

EXAMPLES

Example 1

Preparation of Mono-Sodium Ethylene Glycolate in Ethylene Glycol 300 ml of toluene and 600 ml of ethylene glycol were introduced initially under nitrogen, and then 35.2 g (0.88 mol) of sodium hydroxide were added. The mixture was heated to 102° C., and water was removed via a water separator. After almost complete removal of the water, the total amount of toluene was distilled off, giving 586 g of a 12.6% strength mono-sodium ethylene glycolate solution in ethylene glycol with a water content of about 0.1%.

Example 2

Preparation of 2-(2',4'-dinitrophenoxy)-Ethanol Using the Mono-Sodium Ethylene Glycolate Solution in Ethylene Glycol From Example 1

400 ml of ethylene glycol were introduced initially under nitrogen and heated to 65° C. in a 2 l reaction vessel fitted with a stirrer. 162 g of molten 2,4-dinitrochlorobenzene and 586 g of the 12.6% strength mono-sodium ethylene glycolate solution in ethylene glycol obtained in Example 1 were metered in to this mixture simultaneously over the course of 5 hours. The mixture was then stirred for 1 hour at 65° C., and then 600 ml of water was added thereto. The precipitate which formed was filtered off and washed with 1000 ml of water and dried, giving 165.3 g of 2-(2',4'-dinitro-phenoxy)-ethanol in a purity of 99.2%. Hence, a yield of 96.6% is achieved based on 2,4-dinitrochlorobenzene.

Example 3

Preparation of Mono-Potassium Ethylene Glycolate in Ethylene Glycol 200 ml of toluene and 600 ml of ethylene glycol were introduced initially under nitrogen, and then 49.4 g of potassium hydroxide were added. The mixture was heated to 102° C., and water was removed via a water separator. Following actual complete removal of the water, the total amount of toluene was distilled off, giving 578 g of a 15.2% strength mono-potassium ethylene glycolate solution in ethylene glycol having a water content of about 0.02%.

Example 4

Preparation of 2-(2',4'-dinitrophenoxy)-Ethanol Using the Mono-Potassium Ethylene Glycolate Solution From Example 3

200 ml of ethylene glycol and 40 ml of the mono-potassium ethylene glycolate solution prepared under Example 3 were introduced initially under nitrogen and were heated to 65° C. in a 2 l reaction vessel fitted with a stirrer. Over the course of 5 h, 162 g of molten 2,4-dinitro-chlorobenzene and the remainder of the mono-potassium ethylene glycolate solution in ethylene glycol were simultaneously metered in. The mixture was then stirred for one hour at 65° C., and then 600 ml of water were added. The precipitate which formed was filtered off and washed with 1000 ml of water and dried, giving 169.7 g of 2-(2',4'-dinitrophenoxy)-ethanol in a purity of 92%. Hence, a yield of 92% is achieved based on 2,4-dinitrochlorobenzene.

Example 5

Preparation of 2-(2',4'-dinitrophenoxy)-Ethanol Using a Solution of 2,4-dinitrochlorobenzene in N, N-dimethylacetamide 200 ml of ethylene glycol and 40 ml of a 14.4% strength mono-sodium ethylene glycolate solution were introduced initially under nitrogen and were heated to 65° C. in a 2 l reaction vessel fitted with a stirrer. Over the course of 5 h, 162 g of molten 2,4-dinitrochlorbenzene and a further 480 ml of a 14.4% strength mono-sodium ethylene glycolate solution in ethylene glycol were simultaneously metered in. The mixture was then stirred for one hour at 65° C., and then 600 ml of water were added. The precipitate which formed was filtered off and washed with 1000 ml of water and dried, giving 161.3 g of 2-(2',4'-dinitrophenoxy)-ethanol in a purity of 97%. Hence, a yield of 92.2% is achieved based on 2,4-dinitrochloro-benzene.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a 1-substituted 2,4-dinitrobenzene of the formula (I)

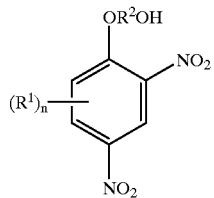

(I)

wherein each $R^1$ is a component comprising a member selected from the group consisting of linear $C_1$–$C_{20}$-alkyl groups, branched $C_1$–$C_{20}$-alkyl groups, $C_6$–$C_{18}$-aryl groups, $C_2$–$C_{20}$-acyl groups, COOH groups, $COOR^3$ groups, in which $R^3$ is a linear or a branched $C_1$–$C_{20}$-alkyl radical, a $SO_3H$ group, or a $SO_3R^4$ group, in which $R^4$ is a linear or a branched $C_1$–$C_{20}$-alkyl radical or a $C_6$–$C_{18}$-aryl radical in which one or more carbon atoms are optionally replaced by O, S or N, or $N(R^5)_2$, in which each $R^5$ is hydrogen, a linear or a branched $C_1$–$C_{20}$-alkyl radical or a $C_2$–$C_{20}$-acyl radical, n is an integer from 0 to 3, and $R^2$ is a radical of the formula (II)

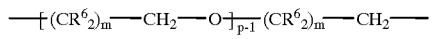

(II)

in which each $R_5$ is hydrogen or a $C_1$–$C_5$-alkyl radical, m is an integer from 1 to 12 and p is an integer from 1 to 4, or $R^6$ is a radical of the formula (III),

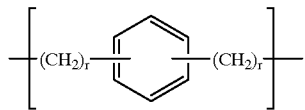

(III)

in which each r is an integer from 0 to 2 and one or more carbon atoms of the phenyl ring are optionally replaced by N, O or S; the process comprising the step of reacting:

A) a 1-halogeno-2,4-dinitrobenzenes of the formula (IV)

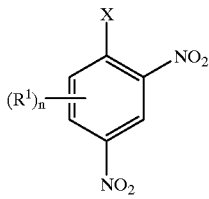

(IV)

in which X is halogen, and $R^1$ and n have the meanings given for the formula (I), with B) a mono-alkali metal salt of a diol of the formula (V)

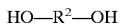  (V)

in which $R^2$ has the meaning given for the formula (I); wherein the halogeno-2,4-dinitrobenzene of the formula (IV) and the mono-alkali metal salt of the diol of the formula (V) are simultaneously added and reacted.

2. The process of claim 1, wherein in formula (IV), X is fluorine, chlorine, bromine or iodine.

3. The process of claim 1, wherein in formula (IV), each $R^1$ is a component comprising a member that is selected from the group consisting of linear $C_1$–$C_{10}$-alkyl groups, branched $C_1$–$C_{10}$-alkyl groups, $C_6$–$C_{12}$-aryl groups, $C_2$–$C_6$-acyl groups, $N(R^5)_2$ groups in which each $R^5$ is hydrogen, a linear or a branched $C_1$–$C_6$-alkyl radical or a $C_2$–$C_6$-acyl radical, and independently thereof n is 0, 1 or 2.

4. The process of claim 1, wherein in the formula (V), each $R^2$ is a radical of the formula (II) in which m is an integer from 1 to 9, $R^6$ is hydrogen or methyl and p is 1 or 2.

5. The process of claim 4, wherein m is 1, 2 or 3.

6. The process of claim 4, wherein in the formula (V), each $R^2$ is —[$CH_2$—$CH_2$]—, —[$CH(CH_3)$—$CH_2$]— or —[$CH_2$—$C(CH_3)_2$—$CH_2$]—.

7. The process of claim 1, wherein the mono-alkali metal salt of the diol of the formula (V) is a component comprising a member selected from the group consisting of mono-sodium salts, mono-potassium salts and mono-caesium salts.

8. The process of claim 7, wherein the mono-alkali metal salts of the diol of the formula (V) are a component comprising a member selected from the group consisting of mono-potassium ethylene glycolate and mono-sodium ethylene glycolate.

9. The process of claim 1, wherein the mono-alkali metal salt of the diol of the formula (V) is used with a solvent as a mixture.

10. The process of claim 9, wherein the solvent is a diol of the formula (V) and the mixture that has a water content of less than about 5%.

11. The process of claim 10, wherein the mixture of the mono-alkali metal salt of the diol of the formula (V) and the diol of the formula (V) further comprises an organic solvent comprising a member selected from the group consisting of unsubstituted aliphatic hydrocarbons, substituted aliphatic hydrocarbons, substituted aromatic hydrocarbons, unsubstituted aromatic hydrocarbons, substituted amides and unsubstituted amides.

12. The process of claim 9, wherein the mixture has a water content that is less than about 2%.

13. The process of claim 12, wherein the mixture has a water content that is less than about 0.2%.

14. The process of claim 1, wherein the simultaneous addition of the 1-halogeno-2,4-dinitrobenzene of the formula (IV) and the mono-alkali metal salt of the diol of the formula (V) is a simultaneously metered addition and is carried out such that, per unit time, either the 1-halogeno-2,4-dinitrobenzene of the formula (IV) or the mono-alkali metal salt of the diol of the formula (V) is metered in an excess of up to about 20 mol %, based on the other compound in each case.

15. The process of claim 1, wherein the simultaneous addition of the 1-halogeno-2,4-dinitrobenzene of the formula (IV) and the mono-alkali metal salt of the diol of the formula (V) is ) is a simultaneously metered addition and is carried out such that, per unit time, either the 1-halogeno-2,4-dinitrobenzene of the formula (IV) or the mono-alkali metal salt of the diol of the formula (V) is metered in an excess of up to about 10 mol %.

16. The process of claim 15, wherein the simultaneous addition of the 1-halogeno-2,4-dinitrobenzene of the formula (IV) and the mono-alkali metal salt of the diol of the formula (V) is carried out such that, per unit time, either the 1-halogeno-2,4-dinitrobenzene of the formula (IV) or the mono-alkali metal salt of the diol of the formula (V) is metered in an excess of up to about 5 mol %.

17. The process of claim 1, wherein up to about 20 mol % of the mono-alkali metal salt of the diol of the formula (V) is introduced as an initial charge.

18. The process of claim 1, wherein up to about 10 mol % of the mono-alkali metal salt of the diol of the formula (V) is introduced as an initial charge.

19. The process of claim 1, wherein up to about 5 mol % of the mono-alkali metal salt of the diol of the formula (V) is introduced as the initial charge.

* * * * *